(12) United States Patent
Miyake et al.

(10) Patent No.: US 10,143,761 B2
(45) Date of Patent: Dec. 4, 2018

(54) METHOD FOR CHANGING CONDITION OF AN EYELID FOR EVALUATION OF AN EYELID DISEASE INVOLVING PLUGGING OF MEIBOMIAN GLAND ORIFICES AND/OR TELANGIECTASIA BY ADMINISTRATION OF COMPLETE FREUND'S ADJUVANT

(71) Applicant: SANTEN PHARMACEUTICAL CO., LTD., Osaka-shi (JP)

(72) Inventors: Hideki Miyake, Ikoma (JP); Tomoko Oda, Ikoma (JP)

(73) Assignee: SANTEN PHARMACEUTICAL CO., LTD., Osaka-Shi, Osaka (JP)

( * ) Notice: Subject to any disclaimer, the term of this patent is extended or adjusted under 35 U.S.C. 154(b) by 0 days.

(21) Appl. No.: 14/401,859

(22) PCT Filed: Jun. 18, 2013

(86) PCT No.: PCT/JP2013/066703
§ 371 (c)(1),
(2) Date: Nov. 18, 2014

(87) PCT Pub. No.: WO2013/191168
PCT Pub. Date: Dec. 27, 2013

(65) Prior Publication Data
US 2015/0125395 A1  May 7, 2015

(30) Foreign Application Priority Data
Jun. 19, 2012 (JP) .............. 2012-137779

(51) Int. Cl.
*A61K 31/7048* (2006.01)
*A61K 9/00* (2006.01)
*A61K 49/00* (2006.01)
*A01K 67/027* (2006.01)
*G01N 33/53* (2006.01)
*A61B 3/12* (2006.01)
*G01N 33/50* (2006.01)
*A61K 35/04* (2006.01)
*A61K 35/74* (2015.01)
*G01N 33/15* (2006.01)
*G01N 33/48* (2006.01)
*A61K 31/573* (2006.01)
*A61K 31/7036* (2006.01)

(52) U.S. Cl.
CPC ........ *A61K 49/0008* (2013.01); *A01K 67/027* (2013.01); *A61K 9/0048* (2013.01); *A61K 31/573* (2013.01); *A61K 31/7036* (2013.01); *A61K 35/04* (2013.01); *A61K 35/74* (2013.01); *G01N 33/15* (2013.01); *G01N 33/48* (2013.01); *G01N 33/50* (2013.01); *G01N 33/5088* (2013.01); *A01K 2227/105* (2013.01); *A01K 2227/107* (2013.01); *A01K 2267/03* (2013.01); *A61B 3/12* (2013.01)

(58) Field of Classification Search
CPC ........ A01K 2227/105; A01K 2227/107; A01K 2267/03; A61K 2039/55566; A61K 35/74; A61K 49/0008; A61K 9/0048; A61K 38/1709; G01N 33/5088
See application file for complete search history.

(56) References Cited

U.S. PATENT DOCUMENTS

| | | | | |
|---|---|---|---|---|
| 9,539,204 B2* | 1/2017 | Kido | | A61K 47/06 |
| 2008/0020064 A1* | 1/2008 | Gilbard | | A01N 59/00 |
| | | | | 424/661 |
| 2010/0160250 A1* | 6/2010 | Douglass, III | | A61K 31/7076 |
| | | | | 514/46 |
| 2011/0223169 A1 | 9/2011 | Stern et al. | | |
| 2014/0255355 A1* | 9/2014 | Sing | | A61K 38/19 |
| | | | | 424/93.7 |
| 2015/0245994 A1* | 9/2015 | Kido | | A61K 31/7048 |
| | | | | 514/29 |
| 2016/0022648 A1* | 1/2016 | Miyake | | A61K 31/436 |
| | | | | 514/80 |

FOREIGN PATENT DOCUMENTS

| | | | |
|---|---|---|---|
| CA | 2886042 | * | 4/2014 |
| JP | 2008-231123 A | | 10/2008 |
| JP | 2008-263887 A | | 11/2008 |
| WO | WO 2007/058383 A2 | | 5/2007 |

OTHER PUBLICATIONS

McKenna et al. J. Immunol. 2002; 169:5630-5637.*
Roberge et al. Graefes Arch Clin. Exp. Ophthalmol. 1989; 227:67-71, abstract.*
Mondino et al., Invest. Ophthalmol. Vis. Sci.,1991; 32:1854-1863.*
Fukushima et al. Exp. Eye Res. 1997; 65:631-637.*
The ocular surface disorder reference guide fro clinicians (retrieved from the website: www.aoa.org/documents/optometrists/CPG-10.pdf on Mar. 5, 2017).*
Billiau et al. J. Leukoc. Biol. 2001; 70:849-860.*
International Search Report (PCT/ISA/210) dated Sep. 17, 2013, by the Japanese Patent Office as the International Searching Authority for International Application No. PCT/JP2013/066703.
Daisuke Shii et al., "Inhibitory Effects of Cyclosporine a Eye Drops on Symptoms in Late Phase and Delayed-Type Reactions in Allergic Conjuctivitis Models", Biol. Pharm. Bull., vol. 33, No. 8, 2010, pp. 1314-1318.
Shiro Amano et al., "Definition and Diagnostic Criteria for Meibonian Gland Dysfunction", Journal of the Eye, vo. 27, No. 5, 2010, pp. 627-631 (with English Abstract).

(Continued)

*Primary Examiner* — Chang-Yu Wang
(74) *Attorney, Agent, or Firm* — Buchanan, Ingersoll & Rooney PC

(57) ABSTRACT

A method for changing a condition of an eyelid of a mammal excluding a human, a model animal for evaluating a therapeutic or prophylactic effect against an eyelid disease obtained by the method, a method for producing the model animal, a method of screening using the model animal and a substance having a therapeutic or prophylactic effect against an eyelid disease selected by the method of screening, and a therapeutic or prophylactic agent against an eyelid disease containing the substance as an active ingredient.

7 Claims, No Drawings

(56) References Cited

OTHER PUBLICATIONS

Yan-Li Liu et al., "Suppression of Complete Freund's Adjuvant-Induced Adjuvant Arthritis by Cobratoxin", Acta Phamacol Sin, 2009, vol. 30, No. 2, pp. 219-227.
Sengoku et al.: "Effect of FK506 eye drops on late and delayed-type responses in ocular allergy models," Clinical & Experimental Allergy: Journal of the British Society for Allergy and Clinical Immunology, Wiley Interscience, UK, vol. 33, No. 11, Nov. 1, 2003, pp. 1555-1560, XP009187236.
Supplementary Search Report issued by the European Patent Office in corresponding European Patent Application No. 13806819.2 dated Dec. 7, 2015 (6 pages).
Decision to Grant Patent issued by the Japanese Patent Office in corresponding Japanese Patent Application No. 2013-127456 dated Oct. 3, 2017 (6 pages including partial English translation).
Torkildsen et al.: "Evaluation of clinical efficacy and safety of tobramycin/dexamethasone ophthalmic suspension 0.3% /0.05% compared to azithromycin ophthalmic solution 1% in the treatment of moderate to severe acute blepharitis/blepharoconjunctivitis," Current Medical Research and Opinion, vol. 27, No. 1, Jan. 1, 2011, pp. 171-178.
Jackson et al.: "Treatment of blepharitis and blepharoconjunctivitis: comparison of gentamicin-betamethasone, gentamicin alone and placebo," Canadian Journal of Ophthalmology, Canadian Ophthalmological Society, CA, vol. 17, No. 4, Aug. 1, 1982, pp. 153-156.
Extended Search Report issued by the European Patent Office in corresponding European Patent Application No. 13806819.2 dated Mar. 21, 2016 (14 pages).

* cited by examiner

METHOD FOR CHANGING CONDITION OF AN EYELID FOR EVALUATION OF AN EYELID DISEASE INVOLVING PLUGGING OF MEIBOMIAN GLAND ORIFICES AND/OR TELANGIECTASIA BY ADMINISTRATION OF COMPLETE FREUND'S ADJUVANT

BACKGROUND OF THE INVENTION

Field of the Invention

The present invention relates to a method for changing a condition of an eyelid of a mammal excluding a human, a model animal for evaluating a therapeutic or prophylactic effect against an eyelid disease obtained by the method, a method for producing the model animal, a method of screening using the model animal and a substance having a therapeutic or prophylactic effect against an eyelid disease selected by the method of screening, and a therapeutic or prophylactic agent against an eyelid disease containing the substance as an active ingredient.

Description of the Related Art

Meibomian glands, located in the tarsal plate, are sebaceous glands with orifices on the upper and lower lid margins. Lipids secreted from the meibomian glands are distributed over the lid margins and the outermost layer of tears, and serve to inhibit evaporation of the tears, promote tear stability, promote the spread of tears over the ocular surface, and inhibit the flow of tears on the lid margins out to the skin, for example. Abnormal functioning of meibomian glands results in eyelid diseases such as blepharitis, marginal blepharitis, meibomian gland dysfunction, meibomitis, meibomian gland blockage, and the like.

Blepharitis is an inflammatory condition of the eyelid, accompanied by ulceration, itching, and pain, and aggravation thereof results in a loss of eyelashes and thickening of the eyelid. Blepharitis is called differently depending on the affected site: marginal blepharitis or anterior blepharitis occurs mainly around the root of the eyelashes; eyelid dermatitis occurs mainly on the skin of the eyelid; posterior blepharitis develops in an area closer to the conjunctiva than a line connecting the meibomian gland orifices; and angular blepharitis occurs mainly at the outer canthus. Causes of blepharitis include purulent due to an infection with bacteria or the like, atopic, and seborrheic due to oversecretion of the sebaceous glands. Steroids, antibiotics, antihistamines, and the like are used as therapeutic drugs.

Meibomian gland dysfunction refers to abnormal functioning of meibomian glands including exits of lipids. Broadly, there are two types of meibomian gland dysfunction: a decreased secretion-type in which the amount of secreted lipids decreases; and an increased secretion-type in which an excessive amount of lipids are secreted. Causes of meibomian gland dysfunction include primary such as obstructive, atrophic, congenital, and the like; and secondary such as secondary to rosacea, atopy, allergic conjunctivitis, Stevens-Johnson syndrome, graft versus host disease, trachoma, ocular infections, seborrheic dermatitis, contact lens wear, rheumatism, psoriasis, lipid metabolism disorders, cataract surgery, myopia correction surgery, and the like. Meibomian gland dysfunction has various symptoms such as congestion of the eye, foreign body sensation, sensation of dryness, burning sensation, itching, and the like. Antibiotics and the like are used as therapeutic drugs.

On the other hand, complete Freund's adjuvant is used as a potent immunological adjuvant to prepare arthritic model animals (Acta Pharmacol Sin, 2009, 30 (2), 219-227). No report has heretofore been made, however, that considers an influence of administering complete Freund's adjuvant to a mammal on the eyelid.

BRIEF SUMMARY OF THE INVENTION

Creating a therapeutic or prophylactic drug against an eyelid disease essentially requires screening using a model animal with which its therapeutic or prophylactic effect can be evaluated. However, no model animal has heretofore been available with which a therapeutic or prophylactic effect against an eyelid disease can be evaluated.

The present inventors, therefore, conducted extensive research to find a model animal and a method of screening with which a therapeutic or prophylactic effect against an eyelid disease can be evaluated.

Consequently, the inventors surprisingly found that the administration of complete Freund's adjuvant to a mammal causes at least one of plugging of meibomian gland orifices and telangiectasia around meibomian gland orifices. The inventors further found that these conditions can be improved with an existing drug. The inventors then found that a therapeutic or prophylactic effect against an eyelid disease can be evaluated by determining these conditions after administering a test substance, thus accomplishing the present invention.

That is, the present invention relates to the following.

(1) A method for changing a condition of an eyelid by administering complete Freund's adjuvant to a mammal excluding a human.

(2) The method according to item (1) above, wherein a change in the condition of the eyelid is at least one of plugging of meibomian gland orifices and telangiectasia around meibomian gland orifices.

(3) The method according to item (1) above, wherein the mammal is a rodentia or a lagomorpha.

(4) The method according to item (1) above, wherein the mammal is a rat or a rabbit.

(5) The method according to item (1) above, wherein the complete Freund's adjuvant is administered to an upper eyelid.

(6) The method according to item (1) above, wherein an amount of the complete Freund's adjuvant administered is 1 to 300θ.

(7) The method according to item (1) above, wherein a period of 3 days or longer is allow to pass after administering the complete Freund's adjuvant.

(8) A model animal for evaluating a therapeutic or prophylactic effect against an eyelid disease obtained by the method according to any of items (1) to (7) above.

(9) The model animal according to item (8) above, wherein the eyelid disease is at least one of a disease involving plugging of meibomian gland orifices and a disease involving telangiectasia around meibomian gland orifices.

(10) The model animal according to item (8) above, wherein the eyelid disease is blepharitis, marginal blepharitis, meibomian gland dysfunction, meibomitis, or meibomian gland blockage.

(11) A method for producing a model animal for evaluating a therapeutic or prophylactic effect against an eyelid disease by the method according to any of items (1) to (7) above.

(12) A method of screening for a substance having a therapeutic or prophylactic effect against an eyelid disease including administering a test substance to the model animal according to item (8) above, and determining a condition of an eyelid of the model animal.

(13) The method of screening according to item (12) above, wherein the condition of the eyelid is a condition of meibomian glands or therearound.

(14) The method of screening according to item (13) above, wherein the condition of meibomian glands or therearound is at least one of plugging of meibomian gland orifices and telangiectasia around meibomian gland orifices.

(15) The method of screening according to item (12) above, wherein the test substance is instilled into an eye.

(16) A substance having a therapeutic or prophylactic effect against an eyelid disease selected by the method of screening according to item (12) above.

(17) A therapeutic or prophylactic agent against an eyelid disease containing the substance according to item (16) above as an active ingredient.

It should be noted that one or more of the features according to items (1) to (17) above can be selected and combined as appropriate.

According to the present invention, a test substance can be readily evaluated for its therapeutic or prophylactic effect against an eyelid disease.

DETAILED DESCRIPTION OF THE INVENTION

The present invention will be hereinafter described in detail.

The method for changing a condition of an eyelid by administering complete Freund's adjuvant according to the invention has a feature in that the condition of the eyelid is changed by administering complete Freund's adjuvant to a mammal excluding a human. The "mammal" used in the method for changing the condition of the eyelid by administering complete Freund's adjuvant according to the invention excludes a human, but otherwise is not particularly limited, and specific examples of the mammal include a mouse, a rat, a hamster, a guinea pig, a rabbit, a cat, a dog, an ape, and the like. A mouse, a rat, or a rabbit is preferable, and a rat or a rabbit is particularly preferable. The sex, the weeks of age, and the body weight of the mammal are not particularly limited.

As used herein, the term "complete Freund's adjuvant" (CFA) refers to an adjuvant obtained by adding mycobacteria or killed bacteria of *Mycobacterium tuberculosis* to a mixture of paraffin and Arlacel to potentiate the antigenicity. The term "adjuvant" herein refers to a substance that when inoculated into an organism together with an antigen, serves to potentiate the immunoreaction.

The administration of complete Freund's adjuvant according to the present invention is done by administering complete Freund's adjuvant, neat or diluted, to an eyelid, preferably an upper eyelid, preferably by an injection. The amount of complete Freund's adjuvant administered is preferably 1 to 300 µL, more preferably 1 to 200 µL, still more preferably 5 to 100 µL, and particularly preferably 10 to 60 µL, although it can be adjusted as appropriate, depending on the type of the mammal, for example. Complete Freund's adjuvant may be administered in a single dose or a plurality of doses at time intervals, and when it is administered in a plurality of doses, the number of doses is preferably 2 to 5, and more preferably 2 or 3. For a single dose, complete Freund's adjuvant may be administered to one site or a plurality of divided sites, preferably 1 to 5 sites, and more preferably 1 to 3 sites.

A period of 3 days or longer, preferably 5 days or longer, and more preferably 7 days or longer is allowed to pass after the completion of the administration of complete Freund's adjuvant, so as to obtain the model animal according to the invention.

The invention also provides a model animal for evaluating a therapeutic or prophylactic effect against an eyelid disease obtained by the above-described method for changing the condition of the eyelid by administering complete Freund's adjuvant according to the invention. Furthermore, the invention provides a method for producing a model animal for evaluating a therapeutic or prophylactic effect against an eyelid disease obtained by the above-described method for changing the condition of the eyelid by administering complete Freund's adjuvant according to the invention.

As used herein, the term "eyelid disease" refers to a disease that affects an eyelid, and is preferably a disease involving at least one of plugging of meibomian gland orifices and telangiectasia around meibomian gland orifices. Specific examples of the eyelid disease include blepharitis, marginal blepharitis, meibomian gland dysfunction, meibomitis, meibomian gland blockage, and the like.

As used herein, the term "blepharitis" is an inflammatory condition of an eyelid, and includes anterior blepharitis, marginal blepharitis, posterior blepharitis, eyelid dermatitis, angular blepharitis, and the like. Causes of blepharitis include purulent due to an infection with bacteria or the like, atopic, seborrheic, and the like.

As used herein, the term "meibomian gland dysfunction" refers to abnormal functioning of meibomian glands including exits of lipids, and includes the decreased secretion-type in which the amount of secreted lipids decreases, and the increased secretion-type in which an excessive amount of lipids are secreted. Causes of meibomian gland dysfunction include primary such as obstructive, atrophic, congenital, and the like; and secondary such as secondary to rosacea, atopy, allergic conjunctivitis, Stevens-Johnson syndrome, graft versus host disease, trachoma, ocular infections, seborrheic dermatitis, contact lens wear, rheumatism, psoriasis, lipid metabolism disorders, cataract surgery, myopia correction surgery, and the like.

As used herein, the term "meibomitis" is an inflammatory condition of meibomian glands, and the meibomian gland blockage is a condition in which a mixture of keratinized matter and lipids becomes solid within the ducts of meibomian glands.

The present invention also provides a method of screening for a substance having a therapeutic or prophylactic effect against an eyelid disease including administering a test substance to the above-described model animal according to the invention, and determining a condition of an eyelid of the model animal.

Examples of the "test substance" according to the invention include known or novel synthetic or natural compounds. Specific examples of such compounds include aromatic compounds, aliphatic compounds, cyclic or linear peptides, proteins, sugar, nucleic acids and derivatives thereof, salts thereof, and the like.

The test substance according to the invention can be orally or parenterally administered, and is particularly preferably instilled into an eye.

When the test substance is instilled into an eye, the test substance dissolved or suspended in purified water, saline, a buffer, or the like can be administered.

The test substance can also be administered by applying an ophthalmic ointment prepared using a base such as white petrolatum, liquid paraffin, or the like.

When the method of screening according to the invention is carried out, a therapeutic effect of the test substance can be evaluated by administering the test substance to the model animal obtained by administering complete Freund's adjuvant, and then determining the condition of the eyelid of the model animal. On the other hand, a prophylactic effect of the test substance can be evaluated by determining the condition of the eyelid of the model animal concurrently with the production of the model animal or when the test substance has been administered before.

When the method of screening according to the invention is carried out, preferably, the condition of the eyelid of the model animal to which the test substance has been administered is compared with that of a model animal to which a vehicle or saline has been administered. Preferably, as a control, an animal to which complete Freund's adjuvant has not been administered is used.

The evaluation of the therapeutic or prophylactic effect against the eyelid disease according to the invention is conducted by determining the condition of the eyelid of the model animal, preferably, by determining the condition of meibomian glands or therearound, and more preferably, by determining at least one of plugging of meibomian gland orifices and telangiectasia around meibomian gland orifices.

In the case of the evaluation by determining plugging of meibomian gland orifices, the evaluation is preferably made by observing the meibomian gland orifices with the slitlamp or the like, and determining the number of clogged meibomian glands. As used herein, the term "plugging" or "plugged" refers to, for example, the state in which the meibomian gland orifice is clouded in a white or yellowish white color, or the state in which the meibomian gland orifice is opaque and swollen. While a screening reference is not particularly limited and can be set depending on the amount of the test substance administered, the type of the animal used, and the like, the screening reference is preferably such that the average value of the number of plugged meibomian glands for a test substance administered group is smaller than that for a vehicle or saline administered group, and more preferably, the number of plugged meibomian glands for the test substance administered group is significantly smaller than that for the vehicle or saline administered group.

In the case of the evaluation by determining telangiectasia around meibomian gland orifices, the evaluation is preferably made by observing the meibomian gland orifices with the slitlamp or the like, and determining the number of dilated capillary vessels running between meibomian gland orifices. As used herein, the term "dilated capillary vessels" refers to, for example, capillary vessels in such a state that as a result of the expansion of vessel diameters, the capillary vessels, which are otherwise normally invisible, can be seen. While a screening reference is not particularly limited and can be set depending on the amount of the test substance administered, the type of the animal used, and the like, the screening reference is preferably such that the average value of the number of dilated capillary vessels for the test substance administered group is smaller than that for the vehicle or saline administered group, and more preferably, the number of dilated capillary vessels for the test substance administered group is significantly smaller than that for the vehicle or saline administered group.

Furthermore, the invention provides a substance having a therapeutic or prophylactic effect against an eyelid disease selected by the above-described method of screening according to the invention, and a therapeutic or prophylactic agent against an eyelid disease containing the substance as an active ingredient.

Examples

The invention will hereinafter be described in more detail with reference to the Examples, which are provided for better understanding of the invention, and should not to be construed as limiting the scope of the invention.

1. Influence of Administering Complete Freund's Adjuvant on Plugging of Meibomian Gland Orifices and Capillary Vessels Around Meibomian Glands (Experimental Method)

Complete Freund's adjuvant or saline was administered in a dose of 10 μL to an upper eyelid at three sites of each male Japanese albino rabbit weighing approximately 2 kg. On day 7, day 14, and day 21 after the administration, observation was conducted with the slitlamp, and the lid margin of the upper eyelid was equally divided into three sections, i.e., an ear-side section, a central section, and a nose-side section. For each of these sections, a score for each of plugging of meibomian gland orifices and telangiectasia around orifices was determined in accordance with the criteria shown in Tables 1 and 2 below, and a sum of scores for the three sections was calculated as the score per eye. In this experiment, the state in which a meibomian gland orifice was clouded in a white or yellowish white color was identified as the "plugging of the meibomian gland orifice". Moreover, the term "dilated capillary vessels" refers to, for example, capillary vessels in such a state that as a result of the expansion of vessel diameters, the capillary vessels, which are otherwise normally invisible, can be seen.

TABLE 1

| Score | Plugged Condition of Meibomian Gland Orifices |
|---|---|
| 0 | No plugging of meibomian gland orifices is observed with the eyelid open. |
| 1 | Plugging of meibomian gland orifices is observed with the eyelid open; the number of plugged meibomian gland orifices is 3 or less. |
| 2 | Plugging of meibomian gland orifices is observed with the eyelid open; the number of plugged meibomian gland orifices is 4 to 6. |
| 3 | Plugging of meibomian gland orifices is observed with the eyelid open; the number of plugged meibomian gland orifices is 7 or more. |

TABLE 2

| Score | Condition of Telangiectasia around Meibomian Gland Orifices |
|---|---|
| 0 | No dilation of capillary vessels is observed around meibomian gland orifices with the eyelid open. |
| 1 | Capillary vessels around meibomian gland orifices are slightly dilated with the eyelid open, and the capillary vessels are sparsely distributed. |
| 2 | Capillary vessels around meibomian gland orifices are dilated to an intermediate level with the eyelid open, and some capillary vessels are densely distributed. |
| 3 | Capillary vessels around meibomian gland orifices are dilated to an advanced level with the eyelid open, and the capillary vessels are densely distributed. |

(Results and Discussion)

Table 3 shows the results of scores for plugging of meibomian gland orifices (8 rabbits for each group), and Table 4 shows the results of scores for telangiectasia around meibomian gland orifices (8 rabbits for each group).

TABLE 3

| | Saline Administered Group (Average Value) | CFA Administered Group (Average Value) |
|---|---|---|
| Day 7 | 0.6 | 3.0 |
| Day 14 | 0.5 | 4.4 |
| Day 21 | 0.7 | 5.6 |

TABLE 4

| | Saline Administered Group (Average Value) | CFA Administered Group (Average Value) |
|---|---|---|
| Day 7 | 0.1 | 2.6 |
| Day 14 | 0.1 | 4.5 |
| Day 21 | 0.1 | 5.2 |

On each of day 7, day 14, and day 21 after the administration of complete Freund's adjuvant, an increase in the score for plugging of meibomian gland orifices and an increase in the score for telangiectasia were observed in the complete Freund's adjuvant administered group, as compared to the saline administered group.

2. Examination of Effect of Therapeutic Drug (Rabbits)

(Experimental Method)

Complete Freund's adjuvant was administered in a dose of 10 µL to an upper eyelid at three sites of each male Japanese albino rabbit weighing approximately 2 kg. On day 4 of the initiation, the meibomian gland orifices and therearound of the right upper eyelid were observed with the slitlamp, and scores were determined. The scores were determined in accordance with the criteria shown in Tables 1 and 2 below. Rabbits were divided into a saline administered group and a TOBRADEX® ST (0.3% tobramycin, 0.05% dexamethasone) administered group (8 rabbits for each group), so as to reduce variations in the average value of each of the scores. From day 5 of the initiation, saline or TOBRADEX® ST ophthalmic solution was instilled into right eyes for 10 days (50 µL/eye, 4 doses a day). On day 11 and day 15 of the initiation, the meibomian gland orifices and therearound of right upper lid margins were observed with the slitlamp, and scores were determined. Table 5 shows the results of scores for plugging of meibomian gland orifices, and Table 6 shows the results of scores for telangiectasia around meibomian gland orifices.

TABLE 5

| | Saline Administered Group (Average Value) | TOBRADEX® ST Ophthalmic Solution Administered Group (Average Value) |
|---|---|---|
| Day 4 | 0.9 | 0.9 |
| Day 11 | 2.6 | 1.4 |
| Day 15 | 3.7 | 1.7 |

TABLE 6

| | Saline Administered Group (Average Value) | TOBRADEX® ST Ophthalmic Solution Administered Group (Average Value) |
|---|---|---|
| Day 4 | 1.3 | 1.1 |
| Day 11 | 2.9 | 0.7 |
| Day 15 | 3.0 | 1.1 |

(Results and Discussion)

It was revealed that for the TOBRADEX® ST ophthalmic solution administered group, the score for plugging of meibomian gland orifices and the score for telangiectasia were clearly improved as compared to those for the saline administered group, showing that the test system according to the invention enables evaluation of drug efficacy.

3. Examination of Effect of Therapeutic Drug (Rats)

(Experimental Method)

Complete Freund's adjuvant was administered in a dose of 25 µL to an upper eyelid at one site of each 5-week-old female Lewis rat. On day 7 of the initiation, areas around the meibomian gland orifices of the right upper eyelid were observed with the slitlamp, and a score for telangiectasia was determined. The score for telangiectasia was determined in accordance with the criteria shown in Table 7 below. Rats were divided into a saline administered group and a RINDERON® ophthalmic, otic and nasal solution 0.1% (0.1% betamethasone sodium phosphate) administered group (5 or 6 eyes for each group), so as to reduce variations in the average value of each of the scores. From day 8 of the initiation, saline (5 µL/eye, 4 doses a day) or RINDERON® ophthalmic, otic and nasal solution 0.1% (5 µL/eye, two doses or one dose a day) was instilled into right eyes for 21 days. On day 14, day 21, and day 28 of the initiation, areas around the meibomian gland orifices of each right upper eyelid were observed with the slitlamp, and scores were determined.

TABLE 7

Score Condition of Telangiectasia around Meibomian Gland Orifices

| | |
|---|---|
| 0 | No dilation of capillary vessels around meibomian gland orifices is observed with the eyelid open. |
| 1 | Dilation of several capillary vessels is observed around meibomian gland orifices with the eyelid open. |
| 2 | An intermediate level of dilation of capillary vessels, or slight redness is observed around meibomian gland orifices with the eyelid open. |
| 3 | Redness and an advanced level of dilation of capillary vessels are observed around meibomian gland orifices with the eyelid open. |

(Results and Discussion)

Table 8 shows the results of scores for telangiectasia around meibomian gland orifices.

TABLE 8

| | Saline Administered Group (Average Value) | RINDERON® Ophthalmic, Otic and Nasal Solution 0.1% Administered Group (Average Value) |
|---|---|---|
| Day 7 | 5.7 | 5.8 |
| Day 14 | 5.2 | 4.7 |
| Day 21 | 4.8 | 3.2 |
| Day 28 | 4.2 | 2.7 |

It was revealed that for the RINDERON® ophthalmic, otic and nasal solution 0.1% administered group, the score for telangiectasia was clearly improved as compared to that for the saline administered group, showing that the test system according to the invention enables evaluation of drug efficacy.

According to the invention, a test substance can be readily evaluated for its therapeutic or prophylactic effect against an eyelid disease, and a therapeutic or prophylactic drug against an eyelid disease can be efficiently created.

The invention claimed is:

1. A method for changing a condition of an eyelid for evaluation of an eyelid disease involving plugging of meibomian gland orifices and/or telangiectasia around meibomian gland orifices comprising administering complete Freund's adjuvant in an amount of 1-300 µl to the eyelid of to a mammal excluding a human to induce plugging of meibomian gland orifices and telangiectasia around meibomian gland orifices, wherein the change in the condition of the eyelid is inducing at least one of plugging of meibomian gland orifices and telangiectasia around meibomian gland orifices.

2. The method according to claim 1, wherein the mammal is a rodentia or a lagomorpha.

3. The method according to claim 1, wherein the mammal is a rat or a rabbit.

4. The method according to claim 1, wherein the complete Freund's adjuvant is administered to an upper eyelid.

5. The method according to claim 1, wherein an amount of the complete Freund's adjuvant administered is 5 to 100 µL.

6. The method according to claim 1, wherein a period of 3 days or longer is allowed to pass after administering the complete Freund's adjuvant.

7. A method for producing a model animal for evaluating a therapeutic effect of an agent against an eyelid disease involving at least one of plugging of meibomian gland orifices and telangiectasia around meibomian gland orifices by the method according to claim 1.

* * * * *